(12) United States Patent
Kana et al.

(10) Patent No.: US 10,058,434 B2
(45) Date of Patent: Aug. 28, 2018

(54) COLLAPSIBLE TWO-PIECE OLIF IMPLANT

(71) Applicant: SpineSmith Partners, L.P., Austin, TX (US)

(72) Inventors: Richard J. Kana, Lexington, TX (US); Kevin Dunworth, Austin, TX (US); John B. Rossman, Austin, TX (US); Luis Duarte, San Angelo, TX (US)

(73) Assignee: SpineSmith Partners, L.P., Austin, TX (US)

(*) Notice: Subject to any disclaimer, the term of this patent is extended or adjusted under 35 U.S.C. 154(b) by 420 days.

(21) Appl. No.: 14/645,272

(22) Filed: Mar. 11, 2015

(65) Prior Publication Data

US 2016/0045332 A1 Feb. 18, 2016

Related U.S. Application Data

(60) Provisional application No. 61/951,351, filed on Mar. 11, 2014.

(51) Int. Cl.
*A61F 2/44* (2006.01)
*A61F 2/30* (2006.01)

(52) U.S. Cl.
CPC .. *A61F 2/4455* (2013.01); *A61F 2002/30471* (2013.01); *A61F 2002/30578* (2013.01); *A61F 2002/30579* (2013.01)

(58) Field of Classification Search
CPC .................. A61F 2/4425; A61F 2/4455; A61F 2002/4415; A61F 2002/4475
See application file for complete search history.

(56) References Cited

U.S. PATENT DOCUMENTS

| | | | | |
|---|---|---|---|---|
| 6,193,757 B1* | 2/2001 | Foley | ............... | A61F 2/4455 623/17.16 |
| 6,827,743 B2* | 12/2004 | Eisermann | ............. | A61B 17/68 623/23.54 |
| 2002/0107572 A1* | 8/2002 | Foley | ............... | A61F 2/446 623/17.11 |

* cited by examiner

*Primary Examiner* — Anu Ramana
(74) *Attorney, Agent, or Firm* — Winstead PC

(57) ABSTRACT

The invention is directed to an interbody fusion device comprises a load bearing component and a retention component and further comprises two bone screws that pass through the retention device and into the vertebral bodies. When implanted, the construct is flush with the anterior face of the vertebras and provides support and temporary fixation for the ultimate fusion of the vertebral bodies.

7 Claims, 1 Drawing Sheet

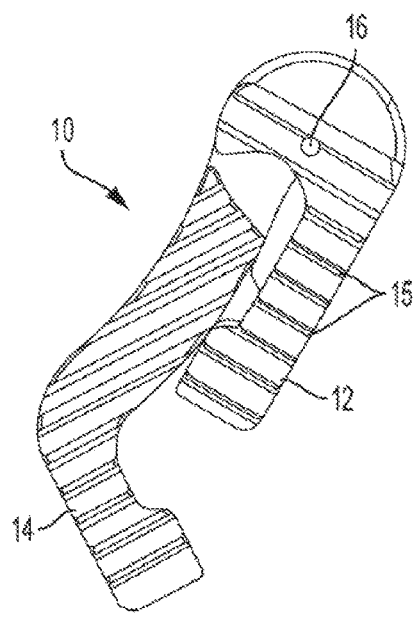
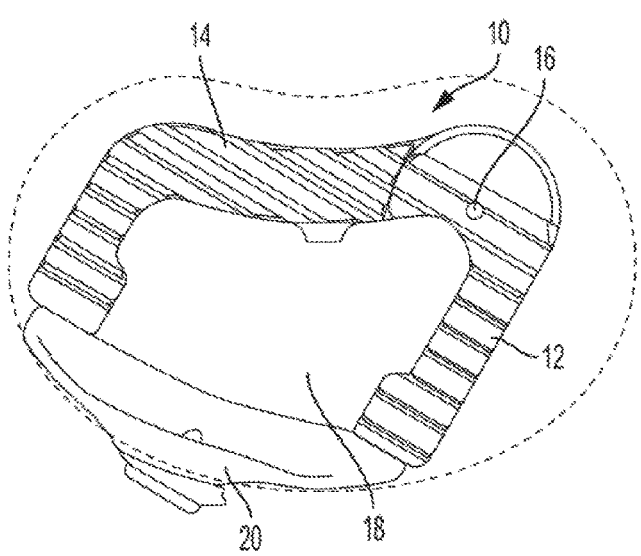
FIG. 1  FIG. 2
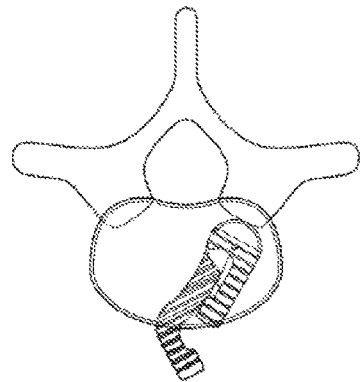
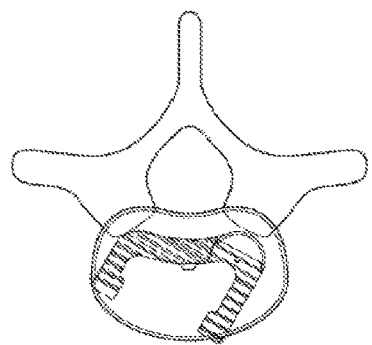
FIG. 3A  FIG. 3B
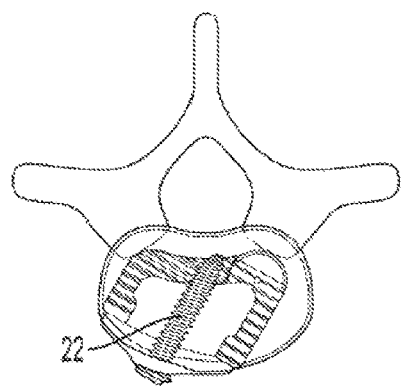
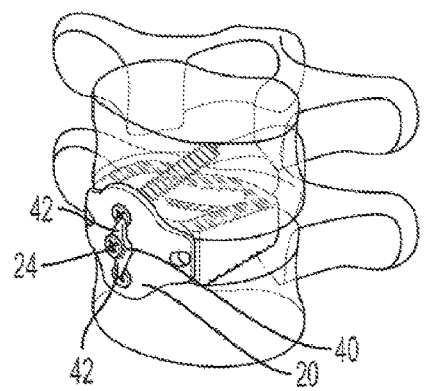
FIG. 3C  FIG. 3D

US 10,058,434 B2

COLLAPSIBLE TWO-PIECE OLIF IMPLANT

CROSS-REFERENCES TO RELATED APPLICATIONS

This Application claims the benefit under 35 U.S.C. § 119(e) of U.S. Provisional Patent Application No. 61/951,351 filed Mar. 11, 2014 which is incorporated herein by reference in its entirety as if fully set forth herein.

BACKGROUND OF THE INVENTION

There is a desire among surgeons to approach the lower lumbar region from an oblique approach, and secondly, a desire to have a more minimally invasive surgical (MIS) procedure.

This approach would locate the patient on their side, vs. flat on their back, as with a typical anterior approach for surgery. A disadvantage to the patient being flat on their back is that all the abdominal organs and vessels must be retracted away to expose the anterior face of the spine. When approaching the spine with the patient on their side, gravity aids in this retraction, naturally pulling the intestines and other vessels out and away from the spine, virtually creating an open space for the surgeon to work within.

MIS is a current buzz word among surgeons. Surgeons want to create the smallest incision possible to complete their procedure because there is less morbidity to the patient and therefore recovery time is faster and overall results are usually better. So, while this oblique approach is desirable, it is also desired to minimize the surgical site. It only makes sense since, the larger the implant, the larger the incision must be to insert it through. The collapsing design of this implant reduces the insertion width to approximately ⅓ of its fully deployed size. This shape and size will enable the option to use dilator tubes vs. an open incision. Dilator tubes only require a very small incision, similar to laparoscopic type procedures.

FIELD OF INVENTION

While the keyword "expandable" is not uncommon among spinal implants, and in fact there are examples that address this function or feature, few address the expandable direction the same as the present invention. The prior art primarily addresses an implant that is expandable in its height. In other words, it may slip in with a 5 mm height requirement and then be expanded to something taller. This may be viewed as a scissor type jack such as that used to elevate an automobile to change a flat tire. This type of expansion is used to control or reestablish the desired disc height, but does not address the issues of the implant footprint size.

An obvious disadvantage with the prior art device is that it does not offer a fully contained area for bone graft material, nor does it offer any form of supplementary or temporary fixation. The 'footprint' or surface area exposed to the bone surface is limited to two relatively thin struts. This means two incisions and two forms of temporary fixation.

Thus, there is a need for a device that can be used with MIS procedures and also offer the ability to form a cavity that can hold bone graft material.

SUMMARY OF THE INVENTION

An embodiment of the invention provides a fusion bearing device that is configured to fit between two adjacent vertebrae, the fusion bearing device having one or more openings to allow access to the end plates of the two adjacent vertebrae, a retention device configured to prevent migration of the fusion bearing device, and one or more fasteners coupled to the retention device to compress the two adjacent vertebrae to the fusion bearing device.

In one embodiment, a spinal fusion device, including a fusion bearing device, is configured to fit between two adjacent vertebrae, the fusion bearing device having an open end, and a retention device configured to couple to the fusion bearing device, at least partially closing the open end.

BRIEF DESCRIPTION OF THE DRAWINGS

FIG. 1 is a diagram of the interbody fusion device in a collapsed state shown in accordance with an embodiment of the invention;

FIG. 2 is a diagram of the interbody fusion device in an expanded state in accordance with an embodiment of the invention;

FIG. 3A shows the interbody fusion device in use in accordance with an embodiment of the invention;

FIG. 3B shows the interbody fusion device in use in accordance with an embodiment of the invention;

FIG. 3C shows the interbody fusion device in use in accordance with an embodiment of the invention; and FIG. 3D shows the interbody fusion device in use in accordance with an embodiment of the invention.

DETAILED DESCRIPTION OF EXEMPLARY EMBODIMENTS

In an embodiment of the invention, the interbody fusion device comprises a fusion bearing device and a retention device and further comprises two bone screws that pass through the retention device and into the vertebral bodies. When implanted, the construct is flush with the anterior face of the vertebras and provides support and temporary fixation for the ultimate fusion of the vertebral bodies.

The present invention relates to spinal fusion implants and related spinal fusion procedures for use in cervical and lumbar applications. One type of spinal fusion is interbody fusion. Typically, an interbody fusion procedure places a bone graft between the vertebrae in the area normally occupied by an intervertebral disc. In preparation for a spinal fusion procedure, the intervertebral disc is removed. A device, typically containing a bone promoting matrix, such as allograph bone, may be placed between the vertebra to maintain spine alignment and disc height. Fusion then occurs between the endplates of the vertebrae. In some examples, fusion is augmented by a process called fixation, meaning the placement of screws, rods and/or plates to stabilize the vertebra to facilitate bone fusion. The present invention provides an interbody fusion device that overcomes problems found in the prior art, such as the angles of the screws, rods and/or plates that are used to stabilize the vertebra.

Generally, the present invention provides a two piece interbody fusion device that may be used to perform anterior lumbar interbody fusion (ALIF). In one example, a first piece of the interbody fusion device is a ring-shaped load bearing device that is designed to bear the axial loading from the end plates of adjacent vertebrae. A second piece of the interbody fusion device is a retention component, which may be attached to the ring-shaped load bearing device, whose function is to prevent migration of the load bearing device and to prevent loss or migration of the bone forming matrix placed therein. One or more fasteners, such as bone screws secure the retention component to the vertebrae above and below the load bearing device. The fasteners cause the end plates of the vertebrae to compress the end plates to the load bearing device to facilitate proper fusion. If desired, the fasteners may include an anti backout mechanism to prevent their migration.

In an embodiment of the invention, the interbody fusion device comprises two arm-like structures that are connected at a hinge joint. In certain embodiments, the hinge joint comprises a pin that connects the two arm-like structures. In a collapsed state, the two arm-like structures contact each other along their side surfaces. In an expanded or extended state, the two arm-like structures form the side and back edges of a load-bearing component of the interbody fusion device.

In an embodiment of the invention, the two arm-like structures are laterally extendible, i.e., when extended along the hinge joint, the two arms extend along a lateral plane, which makes the device easy to position between the end plates of two adjacent vertebrae. In the fully extended state and when placed between an upper end plate and a lower end plate, the lower surfaces of the two arms contact the lower end plate and the upper surfaces of the two arms contact the upper end plate.

FIG. 1 shows an interbody fusion device 10 of the present invention in a collapsed state. The interbody fusion device 10 includes a first arm 12 and a second arm 14 that are connected by a hinge 16.

FIG. 2 shows the interbody fusion device 10 of FIG. 1 in an expanded state. In the expanded state, the first arm 12, second arm 14 and hinge 16 form the back and the side edges of a load-bearing component of the interbody fusion device. When coupled with a retention component 20, the interbody fusion device of the present invention is fully assembled. The interbody fusion device comprises a hollow region 18 which can be filled with a prepared material such as a bone forming matrix to help facilitate fusion of the vertebrae.

FIG. 3A is a view of the interbody fusion device 10, showing the interbody fusion device in a collapsed state. FIG. 3B shows the interbody fusion device 10 in an expanded state where the first arm and second arm are extended to form the back and the side edges of a load-bearing component of the interbody fusion device.

The interbody fusion device 10 also includes a plurality of ridges 15 formed on the top and bottom ends of the device 10. The ridges 15 are angled and pointed in such a way that the ridges 15 help to hold the device 10 to the end plates of the vertebrae to reduce the chance of anterior migration of the implant. If desired, one or more openings (not shown) can be formed in the device 10 to facilitate the attachment of instrumentation devices.

As shown in FIG. 3D, the retention mechanism 20 includes a locking plate 40. The plate 40 has two opposing protrusions 42 that extend outward from the plate 40. A set screw 24 is configured to extend through an opening formed in the plate 40, and thread into the retention component 20. The retention component 20, locking plate 40, and set screw 24 can be pre assembled, such that a surgeon will have a single piece that is attached to the load bearing component. Once the bone screws 22 are installed, the surgeon needs only to turn the set screw 44 with a driver to lock the bone screws in place.

As described above, an interbody fusion device of the present invention is intended to be installed between the end plates of two adjacent vertebrae to facilitate the fusion of the vertebrae. FIG. 3D is an isometric diagram of the interbody fusion device 10 shown in FIG. 2 installed between the end plates of two adjacent vertebrae to facilitate the fusion of the vertebrae. FIG. 3C shows a top view of the interbody fusion device 10 shown in FIG. 1 installed on an end plate of a vertebrae with a bone screw 22 extending into and through the retention component 20. The interbody fusion device 10 provides load bearing support as well as the proper spacing between the vertebrae while fusion of the vertebrae takes place. As described in more detail below, the interbody fusion device 10 is positioned between the end plates of the vertebrae within the vertebral body in the area usually occupied by the intervertebral disc. For clarity, the disc annulus is not shown, so the position of the device 10 can be seen.

Following is an example of how an interbody fusion device of the present invention may be used in an ALIF spinal fusion procedure. As described above, a window is cut in the anterior side of the disc annulus to allow an interbody fusion device to be inserted. Next, the nucleus pulpous is cleaned out to provide room for the interbody fusion device. Next, an interbody fusion device 10 in a collapsed state is inserted between the end plates of the adjacent vertebrae using the appropriate instrumentation (see FIG. 3A). Once the surgeon is satisfied that the load bearing device is in the desired position, the arms of the device 10 are extended. Additionally, the end plates can be prepared using the appropriate instruments (e.g., burrs, gouges, curettes, etc.). Next, the space between the endplates and within the device 18 can be filled with a material that will help to facilitate fusion. Next, the retention component 20 is coupled to the device 10. Once the retention component is in place, the bone screws 22 can be installed through the openings in the retention component and into the vertebrae. As the bone screws 22 are tightened, the vertebrae will compress vertebral bodies onto the device 10, which will help facilitate fusion. Also, since the bone screws 16 secure the retention component 20, and do not directly secure the device 10, the bone screws will not tend to cause the interbody fusion device 10 to migrate. Next, the locking plate 40 is engaged to prevent the bone screws 22 from loosening. As is described in detail below, the surgeon can turn the set screw 44 with driver. The protrusions 42 of the locking plate 40 will then be positioned over the ends of the bone screws 22, preventing the screws 22 from backing out.

The interbody fusion device of the present invention can be made from any desired materials. In one example, the load bearing device is made from PEEK® (or a similar material), bone, metal, or any other structural substitute. If the components of the interbody fusion device are radio lucent (such as with PEEK®), then doctors will be able to monitor the fusion process better with X rays. If desired, one or more radio opaque markers can be embedded into the interbody fusion device, which will show up in an X ray. Since the positions of the markers are known relative to the fusion device, a doctor can determine the position of the fusion device in an X ray by viewing the positions of the markers.

PEEK relative to titanium, is often the desired material to support the load between two vertebral bodies. This is because PEEK more closely mimics the stiffness of bone, whereas a titanium support is much stiffer than bone and is known to cause osteolysis.

A school of thought is that the use of donor bone is the very best load bearing material available. However, at least one major problem with the use of bone is that it is only a spacer/cage. A bone ring is not strong enough to support or house bone screws, which are required to hold the vertebral bodies in place while fusion occurs. Therefore, a secondary device, such as an anterior plate and/or rods and pedicle screws must be used to create the necessary temporary fixation. Because of the closed geometry of a bone ring, any graft material must be loaded prior to implantation and not in-situ. As a result of these additional requirements, the use of a bone ring is not preferred by surgeons.

Understanding this, the retention device is designed to be shorter in height than the fusion bearing device. This design offers the strength of titanium to house the bone screws yet allows full loading only on the PEEK component.

An interbody fusion device of the present invention may be configured to any desired size or shape. In one example, load bearing devices can be provided in multiple thicknesses, allowing a surgeon to select a desired size (e.g., 8.0 mm, 10.0 mm, 12.0 mm, 14.mm, etc.). In the examples shown in the figures, the load bearing device has about 5° of lordosis. Of course any desired angle could be used.

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:

1. A spinal fusion device comprising:
   a load bearing component configured to fit between two adjacent vertebrae, the load bearing component comprising a first arm and a second arm that are connected to one another by a hinge joint that allows the load bearing component to be positioned in a collapsed state and an expanded state, the load bearing component having one or more openings to allow access to end plates of the two adjacent vertebrae;
   a retention component that attaches at a first end of the retention component to a first end of the first arm and at a second end of the retention component to a first end of the second arm;
   a locking plate coupled to the retention component; and
   at least one fastener, each fastener configured to couple the retention component to couple the retention component to one of the two adjacent vertebrae.

2. The spinal fusion device of claim 1, wherein the at least one fastener is a bone screw.

3. The spinal fusion device of claim 1, wherein the one or more openings in the load bearing component are adapted for receiving a fusion enhancing material.

4. The spinal fusion device of claim 1, wherein the load bearing component comprises allograft (donor) bone and the retention component comprises titanium.

5. The spinal fusion device of claim 1, wherein the first arm forms a side edge of the load bearing component and the second arm forms a back edge of the load bearing component.

6. The spinal fusion device of claim 1, wherein the locking plate comprises two opposing protrusions that are adapted to keep the at least one fastener in place.

7. The spinal fusion device of claim 1, wherein the load bearing component comprises a plurality of ridges on top and bottom surfaces of the load bearing device.

* * * * *